United States Patent [19]
Dishart

[11] Patent Number: 5,908,822
[45] Date of Patent: Jun. 1, 1999

[54] COMPOSITIONS AND PROCESSES FOR DRYING SUBSTRATES

[75] Inventor: Kenneth T. Dishart, Wilmington, Del.

[73] Assignee: E. I. du Pont de Nemours and Company, Wilmington, Del.

[21] Appl. No.: 08/959,612

[22] Filed: Oct. 28, 1997

[51] Int. Cl.$^6$ .............................. C11D 3/06; C11D 3/30; C11D 3/24
[52] U.S. Cl. .............................. 510/467; 510/499; 134/2
[58] Field of Search .................................... 510/467–499; 134/2; 564/463

[56] References Cited

U.S. PATENT DOCUMENTS

| | | | |
|---|---|---|---|
| 5,514,301 | 5/1996 | Bil et al. | 252/545 |
| 5,610,128 | 3/1997 | Zyhowski et al. | 510/288 |

FOREIGN PATENT DOCUMENTS

| | | |
|---|---|---|
| 52-114623 | 9/1977 | Japan . |
| 3-91566 | 4/1991 | Japan . |
| 7-244839 | 9/1995 | Japan . |

OTHER PUBLICATIONS

CAS and Derwent Abstracts for JP 7–244,839, JP 3–91566 and JP 52–114,623.

*Primary Examiner*—John R. Hardee

[57] ABSTRACT

Novel surfactants and drying and/or cleaning compositions containing such surfactants are disclosed. The surfactants are 1:1 primary or secondary amine salts of γω-perfluoro-$C_6$-$C_{\gamma 8}$-alkyl dihydrogen phosphates and bis(y,co-perfluoro-$C_6$-Cis-alkyl) hydrogen phosphates. The surfactants are soluble in, and convert halocarbons, especially HFC 43-10mee (1,1,1,2,2,3,4,5,5,5-decafluoropentane), into highly effective displacement drying and/or cleaning compositions. These compositions have the ability to remove water or aqueous films from the surface of a broad range of substrates.

13 Claims, No Drawings

COMPOSITIONS AND PROCESSES FOR DRYING SUBSTRATES

FIELD OF THE INVENTION

The present invention relates to novel surfactants and dewatering and cleaning compositions utilizing such surfactants. More particularly, the present invention relates to fluorinated surfactants and dewatering compositions comprising halocarbon solvent and fluorinated surfactants.

BACKGROUND OF THE INVENTION

Many industries use aqueous compositions for the surface treatment of metals, ceramics, glasses, and plastics. Cleaning, plating, and deposition of coatings are often carried out in aqueous media and are usually followed by a step in which residual water is removed. Hot air drying, centrifugal drying, and solvent-based water displacement are common methods used to remove such residual water.

For many years, 1,1,2-trichlorotrifluoroethane (CFC-113) has been the preferred solvent in cleaning and drying or dewatering applications. Recently, chlorofluorocarbons (CFCs) such as CFC-113 have come under regulation as they are believed to contribute to depletion of the earth's stratospheric ozone layer. These regulations have reduced and phased-out the production of CFCs and thereby their release into the earth's atmosphere. Thus, there is a continuing industry need for alternatives to CFC-based compositions.

Hydrofluorocarbons (BFCs) have been proposed as replacements for CFCs in cleaning and drying compositions. Illustrative of such HFC compositions are those described in U.S. Pat. Nos. 5,578,137, 5,514,301, and 5,610,128. Many HFCs have limited solvency for water and hydrocarbon oils and soldering flux residues. The use of surfactant which assists in removal of such materials from substrates is therefore necessary in many drying and cleaning applications of HFCs. Halocarbon solvents containing a hydrophobic surfactant have been used to displace water from substrates. However, identification of an appropriate solvent/surfactant pair to accomplish water displacement and residue cleaning is not trivial.

Many HFCs are unable to dissolve conventional surfactants designed for use with chlorocarbon, chlorofluorocarbon, and hydrochlorofluorocarbon solvents. Not only must surfactants which are soluble in a given HFC be identified, but also those having the desired properties and activity for a given application. It has been a problem in this field to find hydrophobic surfactants that are essentially insoluble in water, will not form an emulsion with water, and yet are still able to displace water or clean process residue from a variety of substrates.

Conventional displacement drying fluids such as Freon® T-DA and Freon® T-DFC marketed by E. I. duPont de Nemours & Co., Wilmington, Del., USA (DuPont), contain low concentrations of highly effective alkyl phosphate amine salt surfactants, such as a 1:1 salt of 2-ethylhexyl amine and isooctyl phosphate, that rapidly release water from surfaces by lowering surface tension. Unfortunately, conventional surfactants such as these are insoluble in HFC solvents.

There is a need in the displacement drying field to find soluble displacement drying surfactants for use in HFC solvents such as 1,1,1,2,2,3,4,5,5,5-decafluoropentane ($CF_3CF_2CFHCFHCF_3$, HFC 43-10mee), which form effective drying compositions at surfactant concentrations of around 0.1 weight percent (wt %) in HFC, and which have very low water solubility.

Certain non-ionic surfactants such as ethoxylated alcohols, mercaptans, or alkylphenols are soluble in HFC 43-10mee. Such surfactants have drying efficiencies of only 50 to 70% of the conventional CFC-113-based drying compositions, require high surfactant concentration which results in substrate rinsing and staining problems, and are water soluble resulting in surfactant loss with the water discharge.

Surprisingly and unexpectedly, it has been discovered that the surfactants of the present invention enhance the performance of HICs such as HFC 43-10mee and other hydrochlorofluorocarbon and hydrofluorocarbon ether halocarbon solvents in displacement drying. The present invention includes a new class of hydrophobic, HFC soluble, fluorinated surfactants with surface activity in HFCs resulting in highly effective displacement drying compositions. More particularly, the present invention includes dewatering and cleaning compositions comprising a HFC solvent and an effective amount of an of a alkylammonium salt of a fluorinated phosphate ester.

Zyhowski et al. in U.S. Pat. No. 5,610,128 disclosed surfactants which are quaternary ammonium salts of alkyl phosphates for use in HFCs for drying and cleaning. Fluoroalkyl groups may be present on the ammonium and/or phosphate ions. The preferred structures have the fluoroalkyl group only on the ammonium ion.

Bil et al. in U.S. Pat. No. 5,514,301 disclosed dewetting or degreasing compositions based on halogenated aliphatic solvents containing in solution at least one mono- or dialkyl phosphate of a fluorinated amine, at least one quaternary ammonium mono- or dialkyl phosphate and optionally a quaternary ammonium chloride.

SUMMARY OF THE INVENTION

The present invention comprises a surfactant composition of the formulae:

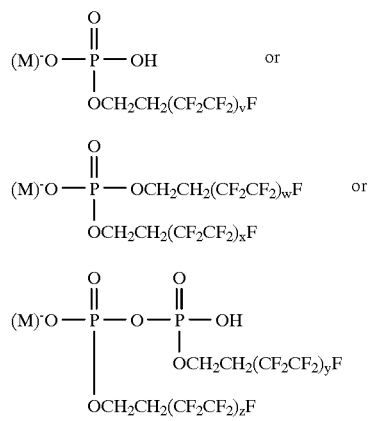

or any combination thereof, wherein M is $^+NH_3R$ or $^+NH_2RR'$, R and R' are independently selected from $C_4$ to $C_{22}$ normal or branched chain alkyl radicals, and v, w, x, y, and z are independently selected from 2 to 8. The present invention further comprises a dewatering and cleaning composition comprising at least one halocarbon solvent and an effective amount of the aforementioned surfactant.

DETAILED DESCRIPTION

The present invention comprises a surfactant of the formulae:

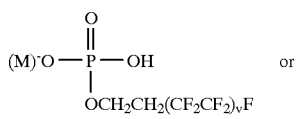

(I)

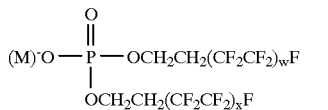

(II)

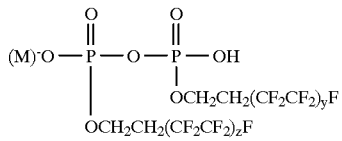

(III)

or any combination thereof, wherein M is:

$^+NH_3R$, wherein R is selected from $C_4$ to $C_{22}$ normal or branched chain alkyl radicals, or $^+NH_2RR'$, wherein R and R' are independently selected from $C_4$ to $C_{22}$ normal or branched chain alkyl radicals. In a preferred embodiment, M is $^+NH_3R$ and R contains a tertiary carbon atom such as those in the Primene® tertiary alkyl-containing primary amines produced by Rohm and Haas Co., Philadelphia, Pa., USA. Preferably, the tertiary center of the tertiary alkyl group is alpha to the primary amine nitrogen and the alkyl group comprises from 12 to 14 carbon atoms.

The variables v, w, x, y, and z are independently selected from 2 to 8. Preferably, v, w, x, y, and z are independently selected from 2 to 5.

The present fluorine containing surfactant may be prepared according to the following scheme.

Step 1: Tetrafluoroethylene (TFE) telomer alcohols of formula $HOCH_2CH_2(CF_2CF_2)_uF$, wherein u is at least 1, are known in the art and may be obtained by procedures such as those disclosed in U.S. Pat. No. 3,875,206, and U.S. Pat. No. 4,587,366, which are herein incorporated by reference. Homologous series of TFE telomer alcohols, e.g., wherein u is from 2 to 8 or from 2 to 5, may be obtained by conventional fractional distillation of mixtures, e.g., wherein u is from 1 to 10. TFE telomer alcohol is allowed to react with phosphorous pentoxide ($P_2O_5$) to produce phosphate esters comprising IV, V, and VI:

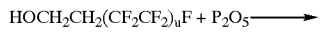

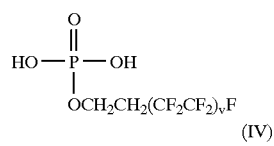

(IV)

+

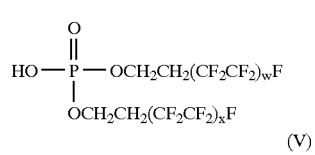

(V)

+

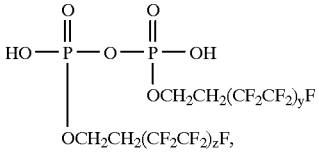

(VI)

wherein v, w, x, y, and z are as defined earlier.

Step 2: Phosphate ester comprising IV, V, and VI is contacted with primary amine $NH_2R$ or secondary amine NHRR', wherein R and R' are as defined earlier, to yield surfactant comprising I, II, and III. By "contacting" of phosphate ester with primary amine is meant that the phosphate ester and the primary amine are allowed to react under conditions which generate surfactant comprising I, II, and III. Preferably, the stochiometery of this reaction is controlled such that in the instance of the diacidic phosphate esters IV and VI, only the first equivalence point is reached, i.e., only one acidic proton on IV and VI is neutralized with amine. The first acid proton on the phosphate ester to be neutralized is a strong acid and results in a salt with a neutral reaction with water, i.e., the salt has a pH in water of about 7. The second acid proton on diacidic phosphate esters IV and VI is a weak acid and neutralization of this second proton occurs at a high pH of around 10. The resulting dibasic salt has an undesirable alkaline reaction in contact with water and also has increased water solubility.

The present invention is also directed to a dewatering composition comprising at least one halocarbon solvent and an effective amount of aforementioned surfactant comprising I, II, or III, or any combination thereof The primary function of the halocarbon solvent is to reduce the amount of water on the surface of a substrate being dried. The primary function of the present surfactant is to displace any remaining water from the surface of the substrate. When the halocarbon solvent and fluorinated surfactant of the present invention are combined, a highly effective displacement drying composition is attained.

Halocarbon solvents of the present invention include hydrochlorofluorocarbons (HCFCs), hydrofluorocarbon ethers (HFEs), and hydrofluorocarbons (HFCs). HCFCs of the present invention comprise $C_jH_{2j+2-k-m}F_kCl_m$ wherein j is from 2 to 5, and k and m are independently selected from 1 to 2j. Preferred from the HCFC halocarbon solvents are HCFC-123 (2,2-dichloro-1,1,1-trifluoroethane), HCFC-141b (1,1-dichloro-1-fluoroethane), HCFC-225ca (3,3-dichloro-1,1,1,2,2-pentafluoropentane), HCFC-225cb (1,3-dichloro-1,1,2,2,3-pentafluoropentane), and isomers thereof. HFEs of the present invention comprise $C_nH_{2n+2-p}F_pO_q$ wherein n is from 5 to 8, p is from 3 to 2n+1, and q<n. Preferred from the HFE halocarbon solvents are perfluorobutyl methyl ether ($C_4F_9OCH_3$), perfluorobutyl ethyl ether ($C_4F_9OC_2H_5$), $C_3F_7OCHF(CF_3)$, $C_3F_7OCF(CF_3)CF_2OCHF(CF_3)$, and isomers thereof. HFCs of the present invention comprise $C_rH_{2r+2-s}F_s$ wherein r is from 3 to 8, and s is from 1 to 2r+1. Preferred the HFC halocarbon solvents are HFC-245ea (1,1,2,3,3-pentafluoropropane), HFC-356mcfq (1,1,1,2,2,4-hexafluorobutane), 1,1,1,2,2,3,3,4,4,5,5,6,6,7,7-pentadecafluoroheptane, HFC-338pcc (1,1,2,2,3,3,4,4-octafluorobutane), HFC 43-10mee (1,1,1,2,2,3,4,5,5,5-decafluoropentane) and isomers thereof Most preferred of the HFCs is HFC-43-10mee.

Many halocarbon solvents of utility in the present invention are available commercially and others may be prepared according to methods commonly known in the art.

Halocarbon solvents of the present invention are preferred to have a normal boiling point of from about 25° C. to about 80° C. More preferred are halocarbon solvents having a normal boiling point of from about 45° C. to about 60° C. Halocarbon solvents with normal boiling points at or near ambient temperature create containment problems when used in conventional design drying and cleaning equipment. High boiling point solvents can be a burn hazard to equipment operators, damage temperature sensitive components, and produce higher energy consumption requirements when employed in conventional design drying and cleaning equipment.

Halocarbon solvents of the present invention are preferably non-flammable by ASTM method D-56-79.

Halocarbon solvents of the present invention are preferably those in which the present fluorinated surfactant is soluble to at least 1 weight % based on the total dewatering composition weight.

The amount of fluorinated surfactant included in the dewatering composition of the present invention can vary widely depending on the particular drying application in which said composition will be used, but is readily apparent to those skilled in the art. Generally, the amount of fluorinated surfactant dissolved in the halocarbon solvent is not greater than about 1 weight % based on the total weight of the surfactant/solvent composition. However, while not economical, larger amounts of surfactant can be used, if after treatment with the composition, the substrate being dried is thereafter treated with halocarbon solvent containing either no or minimal surfactant. The amount of surfactant is at least about 50 parts per million, preferably from about 100 to about 5000 ppm and most preferably from about 200 to about 2000 ppm based on the total weight of the dewatering composition.

As used herein, an effective amount of fluorinated surfactant is any amount which is capable of improving the dewatering performance of a given halocarbon solvent to any extent. Preferably, an effective amount of fluorinated surfactant is that amount which, when present in halocarbon solvent, produces a dewatering composition capable of removing at least 75 wt % of the water present on the surface of a substrate in a single immersion.

The dewatering composition of the present invention is very effective in displacing water from a broad range of substrates including metals, such as tungsten, copper, gold, beryllium, stainless steel, aluminum alloys, brass and the like; from glasses and ceramic surfaces, such as glass, sapphire, borosilicate glass, alumina, silica such as silicon wafers used in electronic circuits, fired alumina and the like; and from plastics such as polyolefin ("Alathon", Rynite®, "Tenite"), polyvinylchloride, polystyrene (Styron), polytetrafluoroethylene (Teflon®), tetrafluoroethylene-ethylene copolymers (Tefzel®), polyvinylidenefluoride ("Kynar"), ionomers (Surlyn®), acrylonitrile-butadiene-styrene polymers (Kralac®), phenol-formaldehyde copolymers, cellulosic ("Ethocel"), epoxy resins, polyacetal (Delrin®), poly(p-phenylene oxide) (Noryl®), polyetherketone ("Ultrapek"), polyetheretherketone ("Victrex"), poly(butylene terephthalate) ("Valox"), polyarylate (Arylon®), liquid crystal polymer, polyimide (Vespel®), polyetherimides ("Ultem"), polyamideimides ("Torlon"), poly(p- phenylene sulfide) ("Rython"), polysulfone ("Udel"), and polyaryl sulfone ("Rydel"). Further, the compositions of the present invention are compatible with elastomers.

The compositions of the present invention do not form noticeable emulsions with the displaced water or form insignificant amounts of such emulsion.

Optionally, additives may be included in the present dewatering compositions. Such additives include compounds having antistatic properties; the ability to dissipate static charge from non-conductive substrates such as glass and silica. Use of an antistatic additive in the dewatering compositions of the present invention may be necessary to prevent spots and stains when drying water or aqueous solutions from electrically non-conductive parts such as glass lenses and mirrors. Most halocarbon solvents of the present invention also have utility as dielectric fluids, i.e., they are poor conductors of electric current and do not easily dissipate static charge. Boiling and general circulation of dewatering compositions in conventional drying and cleaning equipment can create static charge, particularly in the latter stages of the drying process where most of the water has been removed from a substrate. Such static charge collects on non-conductive surfaces of the substrate and prevents the release of the last amount of water which results in water which dries in place resulting in undesirable spots and stains on the substrate. Static charge remaining on substrates can bring out impurities from the cleaning process or can attract impurities such as lint from the air which results in unacceptable cleaning performance. Desirable antistatic additives are polar compounds which are soluble in the present halocarbon solvent and result in an increase in the conductivity of the halocarbon solvent resulting in dissipation of static charge from a substrate. Preferred antistatic additives have a normal boiling point near that of the halocarbon solvent and have minimal to no solubility in water, preferably less than about 0.5 wt % solubility in water. The solubility of antistatic agent is preferably at least 0.5 wt % in halocarbon solvent. The present dewatering composition containing such an antistatic additive is effective in both the drying and rinse steps of the present process. One preferred such antistatic additive is nitromethane ($CH_3NO_2$).

Still further, an optional co-solvent can be used as additive in the dewatering compositions of the present invention. Such co-solvents are desirable where the present dewatering compositions are employed in cleaning conventional process residue from substrates, e.g., removing soldering fluxes and degreasing mechanical components comprising substrates of the present invention. Such co-solvents include alcohols (such as methanol, ethanol, isopropanol), ethers (such as diethyl ether, methyl tertiary-butyl ether), ketones (such as acetone), esters (such as ethyl acetate, methyl dodecanoate, isopropyl myristate and the dimethyl or diisobutyl esters of succinic, glutaric or adipic acids or mixtures thereof), ether alcohols (such as propylene glycol monopropyl ether, dipropylene glycol monobutyl ether, and tripropylene glycol monomethyl ether), and hydrocarbons (such as pentane, cyclopentane, hexane, cyclohexane, heptane, octane), and hydrochlorocarbons (such as trans-1, 2-dichloroethylene). When such a co-solvent is employed with the present dewatering composition for substrate dewatering or cleaning, it may be present in an amount of from about 1% to about 50% percent based on the weight of the overall dewatering composition.

The present invention is also directed to a process for removing at least a portion of water from, i.e., dewatering, the surface of a wetted substrate which comprises contacting the substrate with the aforementioned dewatering composition, and then removing the substrate from contact with the dewatering composition. In the present process, water originally bound to the surface of the substrate is displaced by solvent and/or surfactant and leaves with the dewatering composition. By "at least a portion of water" is meant at least about 75 wt % of water at the surface of a substrate is removed per immersion cycle. By "immersion cycle" is meant one cycle involving at least a step wherein substrate is immersed in the present dewatering composition. Optionally, minimal amounts of surfactant remaining adhered to the substrate can be further removed by contacting the substrate with surfactant-free halocarbon solvent. Holding the article in the solvent vapor or refluxing solvent will further decrease the presence of surfactant remaining on the substrate. Removal of solvent adhering to the surface of the substrate is effected by evaporation. Evaporation of solvent at atmospheric or subatmospheric pressures can be employed and temperatures above and below the boiling point of the halocarbon solvent can be used.

Methods of contacting the substrate with dewatering composition are not critical and can vary widely. For example, the substrate can be immersed in the composition, or the substrate can be sprayed with the composition using conventional equipment. Complete immersion of the substrate is preferred as it generally insures contact between the composition and all exposed surfaces of the substrate. However, any other method which can easily provide such complete contact may be used.

The time period over which substrate and dewatering composition are contacted can vary widely. Usually, the contacting time is up to about 5 minutes, however, longer times may be used if desired. In the dewatering process of the present invention, the contacting time is from about 1 second to about 5 minutes, more preferably the contacting time is from about 15 seconds to about 4 minutes.

Contacting temperatures can also vary widely depending on the boiling point of the composition. In general, the contacting temperature is equal to or less than the composition's normal boiling point.

EXAMPLES

The following examples are included to further teach the present invention and are not intended to limit the present invention.

Example 1

Preparation of Phosphate Ester IV, V and VI (Zonyl® UR BA-LD)

The apparatus consisted of a 2-liter, 3-necked, glass reaction flask equipped with electric heating mantle, thermometer with thermostatic heat controller, mechanical stirrer, and a nitrogen purge. Tetrafluoroethylene telomer alcohol Zonyl® BA-LD ($F(CF_2CF_2)_nCH_2CH_2OH$ wherein n is from 2 to 5) was charged to the reaction flask in the amount of 1566 g (3.3 mol). While stirring and nitrogen purging, the temperature of the alcohol was raised to about 70° C. Phosphorous pentoxide solids, a total of 157 g (1.1 mol), were then added in small increments over a period of 4 hours while maintaining the reaction temperature between 70° C. and 85° C. Stirring of the resultant reaction mixture with nitrogen purge at 80° C. was continued for 24 hours. After this period, the liquid product (Zonyl® UR BA-LD) was transferred to a container for storage, where it solidified to a pale beige, waxy solid.

Example 2

Reaction of Primene® 81 R with Zonyl® UR BA-LD (Example 1 Phosphate Ester)-Preparation of Surfactant (Amines, $C_{12}$-$C_{14}$-tert-alkyl, compnds. with, γω-perfluoro-$C_6$-$C_{12}$-alkyl dihydrozen phosphates (1:1), and Amines, $C_{12}$-$C_{14}$-tert-alkyl, compnds, with bis(γ,ωperfluoro-$C_6$-$C_{12}$-alkyl) hydrogen phosphates)

The Zonyl® UR BA-LD phosphate ester produced in Example 1 was determined by titration to have a first acid number of 72.0 mg KOH/g (at pH 7.0) and a second acid number of 109.4 mg KOH/g (at pH 10). Neutral surfactant corresponds to a surfactant equivalent weight of 779 g/equivalent. Primene® 81 R has a neutralization equivalent weight of 195 g/equivalent. Primene® 81 R is a primary aliphatic amine with branched alkyl chains in which the amino nitrogen atom is bonded to a tertiary carbon to give the tertiary alky grouping:

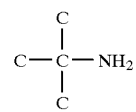

Primene® 81 R consists of mixtures of isomeric amines in the $C_{12}$-$C_{14}$ range. Primene® 81 R was obtained from Rohm and Haas Company, Philadelphia, Pa., USA. Example 1 phosphate ester (40.0 g, 0.051 equivalents) was combined with 12.5 g of isopropyl alcohol. A solution was formed by stirring the mixture and heating at 50° C. The solution was then allowed to cool to room temperature and 10 g (0.051 equivalents) Primene® 81 R was added dropwise with stirring. The resultant mixture was heated at 50° C. and stirred for 15 minutes. The salt product, being 80 wt % surfactant in isopropyl alcohol, was obtained upon cooling and was a clear yellow, moderately viscose liquid.

The present surfactant may be prepared in the absence of alcohol (isopropanol); the resultant surfactant is a viscous, sticky material at room temperature and is difficult to handle and transfer without incurring significant loss of material through holdup on transfer containers and surfaces. Alcohol is used in the present example to facilitate handling and transfer of the product surfactant, as the surfactant produced in the presence of isopropanol is a moderately viscous liquid which is easily transferred with minimal holdup loss on transfer containers and surfaces. Further, such an amount of alcohol in such a surfactant composition, when employed in halocarbon solvent producing a dewatering composition, is found to have no negative effect on the performance of the dewatering and/or cleaning composition. Further, such an amount of alcohol is found to be quickly removed from the present dewatering composition in conventional drying apparatus; the alcohol exits the system with the water being removed from a substrate.

Example 3

Solubility of Surfactant in Halocarbon Solvents

The solubility of various surfactants in halocarbon solvents were determined as follows. Using a glass micropipette, surfactant was added dropwise to a weighed quantity of halocarbon solvent in a glass vial. The pipette was precalibrated for each surfactant to establish the average drop weight. After addition of each drop, the vial was sealed then shaken and the contents visually observed for formation of a homogenous solution (surfactant dissolved). Addition of surfactant was stopped when visual observation revealed that no further surfactant would dissolve (evidenced by formation of a non-homogenous mixture) or the concentration of surfactant in halocarbon solvent reached 10 weight percent.

| Solubilities of Surfactant in HFC 43-10 mee (Vertrel ® XF) | |
| --- | --- |
| Surfactant | Surfactant Solubility in HFC 43-10 mee (g surfactant per 100 g HFC 43-10 mee |
| Zonyl ® UR[a] | <1 (first drop did not completely dissolve) |
| Zonyl ® UR BA-LD | >10 | a; Zonyl ® UR is the reaction product of TFE telomer alcohol $F(CF_2CF_2)_nCH_2CH_2OH$ (wherein n = 2 to 8) with $P_2O_5$ by a procedure identical to that of present Example 1.

| Zonyl ® UR/amine 1:1 salt prepared from amine: | |
| --- | --- |
| n-butyl amine | <1 |
| 2-ethylhexyl amine | >10 |
| Primene ® 81 R | <1 |

| Zonyl ® UR BA-LD/amine 1:1 salt prepared from amine: | |
| --- | --- |
| 2-ethylhexyl amine | <1 |
| Primene ® 81 R | >10 |

| Solubility of Primene ® 81 R/Zonyl ® UR BA-LD 1:1 Salt in Various Halocarbon Solvents | |
| --- | --- |
| | Solubility |
| Halocarbon Solvent | (g Primene ® 81 R/Zonyl ® UR BA-LD 1:1 salt per 100 g halocarbon solvent) |
| HFC 43-10 mee | >10 |
| HCFC-123 ($CHCl_2CF_3$) | >10 |
| HCFC-225 ca/cb ($CF_3CF_2CHCl_2/CF_3ClCF_2CHClF$) (55–58 wt % HCFC-225 ca; 42–45 wt % HCFC-225 cb) | >10 |
| $C_3F_7OCH_3$ (HFE-7100) | >10 |

Example 4

Drying Efficiency Screening

Surfactants were screened in a laboratory bench scale test, which was designed to be of greater drying difficulty than actual practice in order to better differentiate the performance of the different surfactant materials and the concentration levels in the halocarbon solvents. The substrates to be dried were approximately 100 grams of U.S. copper-clad zinc pennies contained in a small 316 stainless steel mesh basket. The basket was designed to comfortably fit into 300 ml tall-form beakers used for weighing and fluid immersion purposes. Each bench scale test consisted of a drying cycle having the steps: (1) obtain the Dry Weight of the basket and pennies; (2) immerse for 1 minute in water with ultrasonic agitation to assure complete wetting and water entrapment; (3) lift basket from the water and allow to drain for 1 minute and then obtain the Wet Weight; (4) immerse in dewatering composition with ultrasonic agitation for 1 minute; (5) transfer the basket to a 60° C. oven for 1 minute to flash vaporize only the halocarbon solvent; (6) weigh the basket and record as Post Dry Weight. The drying efficiency or percent water removed is calculated as follows: [(Wet Wt–Dry Wt)–(Post Dry Wt–Dry W/t)]×100/(Wet Wt—Dry Wt)

After each test cycle the basket and pennies were rinsed with acetone, immersed in boiling isopropyl alcohol and then dried to remove water and any surfactant residue. As a cross check, periodically the water released and floating on top of the drying composition in Step 4 is removed and the volume measured.

The surfactants used in the tests and referred to in the following table are identified by letter code as follows:

A—DuPont Surfactant 621: Dimethyldidodecy quaternary ammonium salt of mono- and di-isooctyl phosphates. Used at 0.033 wt % active ingredient in CFC-113 which constitutes the drying composition marketed by DuPont as Freon® T-DFC.

B—Rhone-Poulenc Alcodet® HSC-1000: Ethylene oxide adduct of dodecyl mercaptan. Used at 0.20 wt % in HFC 43-10mee (Vertrel® XF) which constitutes the drying fluid marketed by DuPont as KCD-9542.

C—2-Ethylhexylamine salt of DuPont Zonyl® UR (1:1 salt)

D—DuPont Zonyl® UR BA-LD

E—Primene® 81 R salt of Zonyl® UR BA-LD (1:1 salt)

The drying test results are tabulated below. The percent water removed values shown are based on five repetitions per test condition.

| Halocarbon Solvent | Surfactant (Wt. %) | % Water Removed | Standard Deviation |
| --- | --- | --- | --- |
| Initial Control Tests: | | | |
| CFC-113 | None | 39 | 5 |
| HFC43-10 mee | None | 36 | 7 |
| Freon ® T-DFC | A (0.033) | 89 | 4 |
| KCD-9542 | B (0.20) | 64 | 1 |
| Zonyl ® UR Salt Tests: | | | |
| HFC 43-10 mee | C (0.008) | 49 | 5 |
| HFC 43-10 mee | C (0.08) | 70 | 4 |
| HFC 43-10 mee | C (0.08) | 63 | 5 |
| HFC 43-10 mee | C (0.16) | 73 | 8 |
| HFC 43-10 mee | C (0.32) | 80 | 6 |
| Additional Control Tests: | | | |
| Freon ® T-DFC | A (0.033) | 95 | 3 |
| KCD-9542 | B (0.20) | 73 | 4 |
| Freon ® T-DFC | A (0.033) | 95 | 4 |
| KCD-9542 | B (0.20) | 72 | 4 |
| HFC 43-10 mee | None | 48 | 3 |
| Zonyl ® UR BA-LD and Salt Tests: | | | |
| HFC 43-10 mee | D (0.1) | 80 | 3 |
| HFC 43-10 mee | D (0.2) | 91 | 4 |
| HFC 43-10 mee | E (0.04) | 75 | 8 |
| HFC 43-10 mee | E (0.08) | 89 | 3 |

Example 5

Commercial Scale Drying Tests

In order to evaluate the performance of a dewatering composition, a small scale drying test was performed in a conventional commercial dryer such as that described in DuPont Technical Bulletin (FREON® Solvent Data Bulletin) number FS-19C titled "Drying with Freon® T-DFC Solvent". A typical commercial dryer has either 2 or 3 sumps with one sump containing the drying composition at its boiling point and the other sump(s) containing pure solvent. The dryer was equipped with a water separator to remove water from the boiling/drying sump and condensing coils to provide containment of the boiling solvent and adequate reflux for vapor phase rinsing of the parts.

During the test, various parts were immersed in water and weighed to determine the degree of water loading. The parts included metallic parts (pennies, stainless steel caps and fuel injector parts) and a glass mirror. The parts were placed in the boiling drying composition for a time of between 30 seconds and 5 minutes. The drying performance was evaluated at a range of times and found to be adequate and essentially the same (less than 2% variability) for immersion times between 30 seconds and 5 minutes.

The parts were allowed to dwell in the vapor above the boiling sump for 30 seconds and then immersed in the rinse sump containing pure solvent for 1 minute and held above the vapor of the rinse sump for 1 minute. The results described below were performed initially with one rinse step and repeated with two rinse steps. Performance was comparable with either 1 or 2 rinse steps. The degree of water removal was measured by weight difference as defined in the present Example 4.

The results shown below are for the surfactant produced in present Example 2 (1:1 salt of Primene® 81 R with Zonyl® UR BA-LD) in halocarbon solvent HFC 43-10mee. The values shown for percent removal were comparable for all parts and showed little variability for the time immersed in the boil sump, therefore the average value is shown. The metallic parts were effectively dried and were not observed to have any visible spots or streak. The glass mirror was observed to have occasional minor spots and streaks.

| Wt % Example 2 Surfactant (Zonyl® UR BA-LD) in HFC 43-10 mee | Wt % Water Removed |
|---|---|
| 0.025 | 99+ |
| 0.05 | 99+ |
| 0.075 | 99+ |
| 0.1 | 99+ |
| 0.2 | 99+ |

Example 6

Commercial Scale Drying Tests—Dewatering Composition Containing Antistatic Additive A number of conventional antistatic additives were tested in halocarbon solvent HFC 43-10mee. By the solubility test in present Example 3, the following conventional antistatic additives were found to be insoluble in HFC-43-10mee: Statis® 450; Zelcon® 5126 and 8037; Zelec® TY, UN, DX, DP, and NK; and Avitex® ML, DN, E, and R. Nitromethane was tested and found to be soluble to greater than 1 wt % in HFC 43-10mee.

Commercial scale drying tests of a glass mirror were carried out in the apparatus of present Example 5 employing present Example 2 surfactant (1:1 salt of Primene® 81 R with Zonyl® UR BA-LD) in HFC 43-10mee and antistatic additive nitromethane.

Non-conductive parts are typically the most difficult to dry and leave with no spots or streaks. The acceptance criteria is visual observation for spots or streaks on the surface of the substrate following the immersion cycle. This may be performed by the naked eye or under a microscope under moderate (5× to 10×) magnification.

The present drying test was performed as described in Example 5. A glass mirror was tested as any spots or stains are readily visible to the naked eye or under moderate magnification. Pennies were also tested to ensure no negative effect resulted from the additional additive on drying performance.

| | Concentration in Drying Sump (wt % in HFC 43-10 mee) | Concentration in Rinsing Sump wt % in HFC 43-10 mee) |
|---|---|---|
| Nitromethane | 0.15–0.5 | 0.10–0.2 |
| Example 2 surfactant (1:1 salt of Primene ® 81 R with Zonyl ® UR BA-LD) | 0.02–0.2 | not detected |

| Drying Performance | Wt % Water Removed | Visual Inspection Results |
|---|---|---|
| Pennies | 99+ | No water present |
| Glass Mirror | 99+ | No water present, no spots or streaks on mirror surface |

Example 6

Dewatering Composition Corrosivity

The corrosivity of the present dewatering composition comprising 0.025—0.1 wt % of present Example 2 surfactant (1:1 salt of Primene 81 R with Zonyl® UR BA-LD) in halocarbon solvent HFC 43-10mee was examined to ensure the present composition would not lead to decomposition of common metals of construction employed in conventional drying and cleaning equipment. To determine this, stainless steel 304 and 316 coupons were placed in the vapor and liquid zones of a small scale dryer and allowed to remain there while the dewatering composition was saturated with water and operating for 2 weeks under reflux conditions. The coupons were visually inspected under 10× magnification and no corrosion was observed.

What is claimed is:

1. A composition comprising at least one halocarbon solvent and from about 50 to about 5000 parts-per-million by weight of a surfactant composition dissolved therein, said surfactant composition comprising surfactant represented by the formulae:

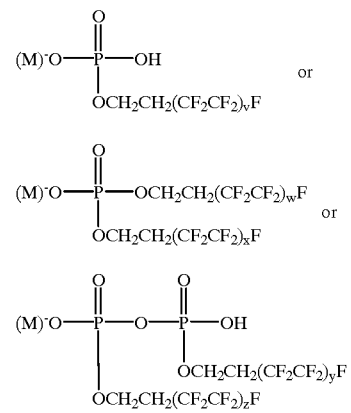

or any combination thereof, wherein M is $^+NH_3R$ or $^+NH_2RR'$, R and R' are independently selected from $C_4$ to $C_{22}$ normal or branched chain alkyl radicals, and v, w, x, y, and z are independently selected from 2 to 8.

2. The composition of claim 1 wherein R and R' are selected from the group consisting of $C_{12}$ to $C_{14}$ hydrocarbon radicals containing at least one tertiary carbon.

3. The composition of claim 1 wherein v, w, x, y, and z are independently selected from 2 to 5.

4. The composition of claim 1 wherein said halocarbon solvent is selected from the group consisting of hydrofluorocarbons, hydrochlorofluorocarbons, and hydrofluorocarbon ethers.

5. The composition of claim 4 wherein said halocarbon solvent is selected from the group consisting of HCFC-123 (2,2-dichloro-1,1,1-trifluoroethane), HCFC-141 b (1,1-dichloro-1-fluoroethane), HCFC-225ca (3,3-dichloro-1,1,1,2,2-pentafluoropentane), HCFC-225cb (1,3-dichloro-1,1,2,2,3-pentafluoropentane), perfluorobutyl methyl ether ($C_4F_9OCH_3$), perfluorobutyl ethyl ether ($C_4F_9OC_2H_5$), $C_3F_7OCHF(CF_3)$, $C_3F_7OCF(CF_3)CF_2OCHF(CF_3)$, HFC-245ea (1,1,2,3,3-pentafluoropropane), HFC-356mcfq (1,1,1,2,2,4-hexafluorobutane), 1,1,1,2,2,3,3,4,4,5,5,6,6,7,7-pentadecafluoroheptane, HFC-338pcc (1,1,2,2,3,3,4,4-octafluorobutane), and HFC 43-10mee (1,1,1,2,2,3,4,5,5,5-decafluoropentane).

6. A dewatering and cleaning composition comprising HFC 43-10mee (1,1,1,2,2,3,4,5,5,5-decafluoropentane) and dissolved therein, from about 50 to about 5000 parts per million by weight, of a surfactant composition of the formulae:

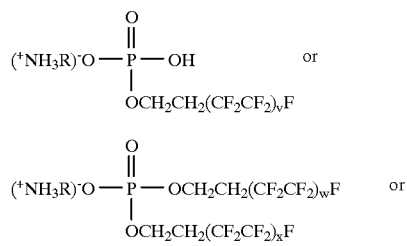

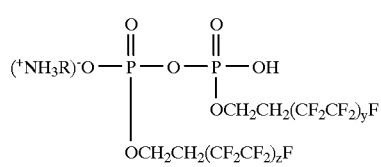

or any combination thereof, wherein R is selected from $C_{12}$ to $C_{14}$ hydrocarbon radicals containing at least one tertiary carbon, and v, w, x, y, and z are independently selected from 2 to 5.

7. The composition of claims 1 or 6 further comprising at least one alcohol.

8. The composition of claim 7 wherein said alcohol consists essentially of isopropyl alcohol.

9. The composition of claims 1 or 6 further comprising at least one antistatic additive.

10. The composition of claim 9 wherein said antistatic additive consists essentially of nitromethane.

11. The composition of claims 1 or 6 further comprising at least one co-solvent selected from the group consisting of alcohols, ethers, ketones, esters, ether alcohols, hydrocarbons, and hydrochlorocarbons.

12. A process for dewatering and/or cleaning a substrate comprising:
    contacting the substrate with the composition of claims 2 or 8, thereby dewatering and/or cleaning said substrate, and
    recovering the dewatered and/or cleaned substrate from the composition.

13. The process of claim 12 wherein said substrate is selected from the group consisting of metals, glasses, ceramics, and plastics.

* * * * *